United States Patent [19]
Aretz et al.

[11] Patent Number: 4,783,404
[45] Date of Patent: Nov. 8, 1988

[54] L-AMINOACID OXIDASE FROM YEASTS OF THE GENUS CRYPTOCOCCUS, THEIR PREPARATION AND USE

[75] Inventors: Werner Aretz, Kelkheim; Klaus Sauber, Bad Soden am Taunus, both of Fed. Rep. of Germany

[73] Assignee: Hoechst Aktiengesellschaft, Fed. Rep. of Germany

[21] Appl. No.: 650,638

[22] Filed: Sep. 14, 1984

[30] Foreign Application Priority Data

Sep. 16, 1983 [DE] Fed. Rep. of Germany ....... 3333453

[51] Int. Cl.$^4$ .......................... C12P 7/62; C12P 7/40; C12P 7/44; C12N 9/06; C12N 1/16
[52] U.S. Cl. ..................................... 435/135; 435/136; 435/143; 435/191; 435/255; 435/911
[58] Field of Search ................ 435/191, 255, 135, 143

[56] References Cited

U.S. PATENT DOCUMENTS

| | | |
|---|---|---|
| 3,791,926 | 2/1974 | Chibata et al. . |
| 3,953,291 | 4/1976 | Chibata et al. . |
| 4,070,348 | 1/1978 | Kraemer et al. . |
| 4,081,327 | 3/1978 | Chibata et al. . |
| 4,357,425 | 11/1982 | Yoshino et al. ..................... 435/191 |

OTHER PUBLICATIONS

Duerre et al., Journal of Bacteriology, vol. 121, No. 2, pp. 656–663, Feb. 1975.

Primary Examiner—Thomas G. Wiseman
Assistant Examiner—Charles L. Patterson, Jr.
Attorney, Agent, or Firm—Finnegan, Henderson, Farabow, Garrett & Dunner

[57] ABSTRACT

Yeasts of the genus cryptococcus, preferably of the species C. Laurentii, form, in the presence of aminoacids, an L-aminoacid oxidase which stereospecifically converts L-aminoacids and their derivatives into the corresponding α-ketoacids. The immobilized cells are advantageously used for this conversion, which can also be used to resolve racemates.

11 Claims, No Drawings

L-AMINOACID OXIDASE FROM YEASTS OF THE GENUS CRYPTOCOCCUS, THEIR PREPARATION AND USE

The invention relates to a new L-aminoacid oxidase having a broad spectrum of substrates, its isolation by fermentation of yeasts of the genus cryptococcus and its use for the preparation of α-ketoacids, their esters and ethers from the corresponding L-α-aminoacids or their derivatives.

L-Aminoacid oxidase, called LAO below, is an inducible enzyme in yeasts of the genus cryptococcus. Thus, to prepare it, the yeasts are fermented with the addition of, as an inducer, an aminoacid or a substance which releases aminoacids. Preferred embodiments of the invention are illustrated in detail below:

The preferred species of genus cryptococcus is *C. laurentii*, for example the strain *Cryptococcus laurentii* var. magnus CBS 569, and the species C. albidus.

The strain *C. laurentii* DSM 2762 is particularly preferred. The starting material for this strain was a sample of soil from Bobodiovlassio (Upper Volta) which was incubated with several transfers, for 2–3 days each time, in a mineral medium containing D-glutamic acid as the only source of nitrogen, at 28° C. These liquid cultures were plated out onto media which contained the ethylamide of D-α-aminoadipic acid as the only N source. After further transfers, the strain DSM 2762, inter alia, was isolated as a pure culture.

This strain is a unicellular, oval yeast which forms neither mycelium nor pseudomycelia. Multiplication takes place by manifold budding; the presence of ascospores or ballistospores has not been detected. The convex, whitish colonies are rough and have a smooth margin. No pigment in the form of carotenoids is produced. Yeast starch was detected with iodine/potassium iodide, both in the colonies and in the liquid cultures. Physiological investigations showed that glucose, sucrose, maltose, raffinose, galactose, lactose, starch, rhamnose, melibiose, dextrin and inositol are assimilated as carbon sources; anaerobic fermentation of the sugars does not take place. Utilization of ammonium sulfate, α-aminoadipic acid, glutamic acid, alanine, leucine, serine, tryptophan, tyrosine and phenylalanine as nitrogen sources has been demonstrated. In contrast, growth with sodium nitrate has not been observed.

It has been found that LAO is formed in parallel with the growth and reaches its highest activity toward the end of the logarithmic phase. Preferred inducers are D-aminoacids, especially D-Leu, D-α-aminoadipic acid (DαAAA) and D-Ala. A survey of the LAO activities found is shown in Table 1:

TABLE 1

| Induction of L-aminoacid oxidase by various aminoacids | | |
|---|---|---|
| N source | OD 546 nm | LAO activity u/g cells* |
| NH₄Cl | 9.5 | 0 |
| D-Ala | 1.9 | 1.22 |
| DL-Ala | 11.8 | 0.93 |
| D-αAAA | 9.3 | 1.50 |
| L-αAAA | 9.0 | 1.25 |
| DL-αAAA | 8.9 | 1.76 |
| D-Leu | 5.0 | 3.70 |
| L-Leu | 6.2 | 1.20 |
| DL-Leu | 4.2 | 1.60 |
| L-Met | 3.1 | 0.70 |
| DL-Phe | 3.6 | 0.74 |
| L-Try | 3.9 | 0.50 |

TABLE 1-continued

| Induction of L-aminoacid oxidase by various aminoacids | | |
|---|---|---|
| N source | OD 546 nm | LAO activity u/g cells* |
| L-Ser | 13.3 | 0.30 |
| D-Glu | 10.2 | 0 |
| DL-Glu | 15.7 | 0 |

*Test substrate L-α-aminoadipic acid (LαAAA)

Preferred C sources are soluble starch and, in particular, lactose and sucrose.

In contrast to the known microbial L-aminoacid oxidases, the LAO according to the invention has a broad spectrum of substrates: apart from most natural aminoacids, other aminoacids such as L-α-aminoadipic acid and L-cephalosporin C are converted into the corresponding α-ketoacids. However, in addition derivatives of the aminoacids are also converted, namely their esters, especially lower alkyl esters and benzyl esters, as well as the ethers, both ethers of the alcohol group of serine and the phenolic hydroxyl group of tyrosine, and thioethers of cysteine. Again, the lower alkyl and benzyl ethers or thioethers are preferred for this. The natural thioether L-methionine is likewise converted.

All the conversions are strictly stereospecific: the L-forms are converted into the corresponding ketoacids or ketoacid derivatives. Thus, according to the invention, it is also possible to resolve racemates, the L-form being converted to the keto derivative while the D-form remains unchanged.

The conversion of the L-aminoacids is advantageously carried out in a pH range from 6.5 to 8.5, advantageously 7–8, in particular 7.5. Thus, suitable buffers are potassium phosphate and tris.HCl buffers.

Advantageous temperatures for the conversion are about 30° to 60°, preferably 40° to 55°, in particular 50° C.

The LAO has a Km value of 0.25 mM and a Vmax of 2 mM for L-α-AAA.

The LAO according to the invention is distinguished by high stability on storage. At 4° C., it is utilizable for several days, and at −18° C., it is utilizable without loss of activity for several months.

The LAO according to the invention is localized on the outer cytoplasmic membrane. The enzyme activity is thus equally high in intact cells which have not been made permeable and in cells treated with cetyltrimethylammonium bromide. Freezing and thawing the cells brings about an activity increase of about 30 to 40%.

The LAO according to the invention can be used as a concentrate from the cytoplasmic membrane. However, the use in the form of immobilized cells is particularly advantageous. Since, as mentioned above, the enzyme is localized on the outer cytoplasmic membrane, it is unnecessary to maintain non-toxic conditions when immobilizing the cells.

In addition to the known advantage of enzyme immobilization—increased stability and ease of manipulation—when the whole cells are embedded isolation and purification of the enzyme is dispensed with.

The immobilization of the enzyme or of the cells can be carried out in a known manner using natural or synthetic polymers (U.S. Pat. Nos. 3,791,926, 3,953,291, 4,070,348 and 4,081,327).

Particularly preferred embodiments of the invention are illustrated in detail in the examples which follow:

EXAMPLE 1

The yeast *Cryptococcus albidus* is maintained on the following solid nutrient media:

| "nutrient broth" | 8 g |
|---|---|
| agar | 15 g |
| dist. water | 1 liter |

The medium is distributed over test tubes and sterilized at 121° C. for 30 min., then cooled, inoculated with the culture and incubated at 25° C. for 3-4 days. The grown culture is rinsed off with 10 ml of sterile saline solution and added to a culture medium of the following composition:

| glucose | 10 g |
|---|---|
| D-α-AAA | 0.3 g |
| $KH_2PO_4$ | 0.875 g |
| $K_2HPO_4$ | 0.125 g |
| NaCl | 0.1 g |
| $MgCl_2.7H_2O$ | 0.5 g |
| $CaCl_2.7H_2O$ | 0.1 g |
| trace element solution | 1 ml |
| vitamin solution | 10 ml |
| dist. $H_2O$ (pH 7.2) | 1 liter |

| Trace element solution: | | Vitamin solution: | |
|---|---|---|---|
| $CoCl_2.6H_2O$ | 0.25 g | biotin | 0.001 g |
| $NiCl_2.6H_2O$ | 0.01 g | vitamin B 12 | 0.005 g |
| $CuCl_2.2H_2O$ | 0.01 g | thiamine.HCl | 0.03 |
| $ZnCl_2$ | 0.1 g | nicotinic acid | 0.035 |
| $H_3BO_3$ | 0.5 g | p-aminobenzoic acid | 0.02 |
| $Na_2MoO_4.2H_2O$ | 0.3 g | pyridoxal.HCl | 0.01 |
| $NaSeO_3.3H_2O$ | 0.1 g | Ca pantothenate | 0.01 |
| $FeSO_4.7H_2O$ | 0.2 g | 50% ethanol | 1 liter |
| dist. $H_2O$ | 1 liter | | |
| (adjusted to pH 2-3 with HCl). | | | |

500 ml of this medium are placed in 2 liter conical flasks and sterilized at 121° C. for 30 min.

The flasks inoculated with a 10 ml inoculum are then incubated at 28° C. and 190 rpm in a rotary shaker. After 72 hours, the grown culture is harvested, washed and taken up in a potassium phosphate buffer (pH 7.5, 50 mM). The LAO activity of the intact cells was determined as 1.34 U/g cells using L-α-AAA as the substrate in an assay dependent on o-phenylenediamine peroxidase.

EXAMPLE 2

*Cryptococcus laurentii* DSM 2762 was cultured by the method of Example 1 in 500 ml of nutrient solution and, after 3 days, transferred into a 12 liter fermenter containing 9 liters of the same medium which, however, contained D-leucine in place of D-α-AAA, and was incubated at 28° C., 400 rpm and an aeration rate of 400 liters of air per hour.

After 4 days, the LAO activity was measured to be 3.5 U/g cells.

EXAMPLE 3

A 6% strength solution of α-carrageenan (Marine Colloids, Rockland, Me., U.S.A.) is made up at 75° C., cooled to 40° C. and mixed with a 4% strength suspension of cryptococcus cells in physiological saline solution in the ratio 1:1. This suspension is injected through a cannula into a precipitation bath (10 mM $CaCl_2$, 300 mM KCl) so that beads are formed. After stirring for one hour, the product is washed with 0.3 M KCl three times. The carrageenan beads are stored at 4° C. in 0.13 M potassium phosphate buffer (pH 7.5) containing 0.02% sodium azide. The activity of the beads is about 80 mU/g wet weight of catalyst.

EXAMPLE 4

10 ml of 10 mM L-phenylalanine, dissolved in 0.1 M potassium phosphate buffer (pH 8.0), are reacted, passing in air at 37° C., with 4 g of *Cryptococcus laurentii* DSM 2762 cells immobilized by the method of Example 3. Addition of 10 μl of technical catalase (Boehringer, Mannheim) brings about the destruction of the resulting hydrogen peroxide and prevents impairment of product quality. The disappearance of the substrate and the formation of the product can be followed by thin-layer chromatography. The product can be detected by spraying the thin-layer chromatogram with 2,4-dinitrophenylhydrazine. Likewise, the formation of ammonium ions can be followed by the nitroprusside method.

The starting material is quantitatively reacted after 5 hours.

The results listed in Tables 2 and 3 below were obtained by the method of Example 4. Unless otherwise indicated, the substrate concentration was 4 mM.

TABLE 2

Substrate spectrum of the LAO from *Cryptococcus laurentii* DSM 2762

| Substrate | LAO activity in % | Substrate | LAO activity in % |
|---|---|---|---|
| L-α-AAA | 100 | D-Ala | 0 |
| L-Ala | 72 | D-α-AAA | 0 |
|  |  | D-Leu | 0 |
| L-Arg | 78 | D-Meth | 0 |
| L-Asn | 68 | D-Phe | 0 |
| L-Asp | >0 | D-Try | 0 |
| L-Cys | >0 | D-Val | 0 |
| L-Glu | 49 |  |  |
| L-Gly | 0 | L-CPC | 76 |
| L-Ile | 40 | D-CPC | 0 |
|  |  | L-Met-amide | 0 |
| L-Leu | 73 | L-Leu amide | 0 |
|  |  | L-Try amide | 0 |
| L-Lys | 34 |  |  |
| L-Met | 58 |  |  |
| L-Phe | 72 |  |  |
| L-Pro | 0 |  |  |
| L-Ser | 46 |  |  |
| L-Thr | 0 |  |  |
| L-Try | 29 |  |  |
| L-Tyr | 56 |  |  |
| L-Val | 0 |  |  |

TABLE 3

Substrate spectrum of the LAO from *Cryptococcus laurentii* DSM 2762

| Substrate | LAO activity in % |
|---|---|
| L-α-AAA | 100 |
| L-Ala—OMe | 98 |
| L-Ala—OEt | 40 |
| L-Ala—OtBu | 32 |
| L-Arg—OMe | 64 |
| L-Leu—OMe | 100 |
| L-Lys—OMe | 109 |
| D,L-Met—OMe | 100 |
| L-Met—OEt | 84 |
| L-Phe—OMe | 116 |
| L-Phe—OEt | 84 |
| L-Phe—OtBu | 69 |
| L-Ser—OMe | 50 |
| L-Ser—OBz | 82 |
| L-(S—Bz)—Cys* | 70 |
| L-(S—Bz)—Cys—OMe** | 63 |
| L-Tyr Me ether** | 74 |
| D,L-Val—OMe | 0 |

TABLE 3-continued

Substrate spectrum of the LAO from *Cryptococcus laurentii* DSM 2762

| Substrate | LAO activity in % |
| --- | --- |
| L-1-naphthylalanine | 63 |
| L-2-naphthylalanine | 100 |

*3 mM
** 2mM
Me = methyl
Et = ethyl
tBu = tert.-butyl
Bz = benzyl

We claim:

1. L-Aminoacid oxidase isolated from a yeast of the genus cryptococcus and having the ability to convert L-alpha-amino-adipic acid and L-cephalosporin C into the corresponding alpha-keto acids.

2. L-Aminoacid oxidase as claimed in claim 1, having a Km value of 0.25 mM and a Vmax of 2 mM for L-alpha-amino-adipic acid.

3. L-Aminoacid oxidase as claimed in claim 1, wherein the yeast is of the species *C. laurentii* or *C. albidus*.

4. L-Aminoacid oxidase as claimed in claim 3, wherein the *C. Laurentii* is the strain DSM 2762.

5. A process for the preparation of the L-aminoacid oxidase as claimed in claim 1, which comprises fermenting the said yeast with the addition of an aminoacid or a substance which releases an aminoacid.

6. The process as claimed in claim 5, wherein the aminoacid is a D-aminoacid.

7. The process as claimed in claim 6, wherein the D-aminoacid is D-Leu, D-Ala, D-α-aminoadipic acid or D-α-aminoadipic acid -α-semiethylamide.

8. The process as claimed in claim 5, wherein the carbon source is lactose or sucrose.

9. A process for the preparation of an α-ketoacid and its esters and ethers which comprises reacting the corresponding L-α-aminoacid or its derivatives with a L-aminoacid oxidase as claimed in claim 1.

10. A process as claimed in claim 9, where the L-aminooxidase is a concentrate from the cytoplasmic membrane or in the form of immobilized cells.

11. A biologically pure culture of *Cryptococcus laurentii* DSM 2762.

* * * * *